(12) United States Patent
Leeper et al.

(10) Patent No.: US 9,920,623 B1
(45) Date of Patent: Mar. 20, 2018

(54) SYSTEMS AND METHODS FOR COLLECTING CUTTING SAMPLES DURING OIL AND GAS DRILLING OPERATIONS

(71) Applicant: Solid Automated Geological Solutions, LLC, Midland, TX (US)

(72) Inventors: Jay Leeper, Midland, TX (US); James Martin, Midland, TX (US)

(73) Assignee: Solid Automated Geological Solutions, LLC, Midland, TX (US)

( * ) Notice: Subject to any disclaimer, the term of this patent is extended or adjusted under 35 U.S.C. 154(b) by 154 days.

(21) Appl. No.: 14/946,242

(22) Filed: Nov. 19, 2015

Related U.S. Application Data

(60) Provisional application No. 62/082,658, filed on Nov. 21, 2014, provisional application No. 62/215,840, filed on Sep. 9, 2015.

(51) Int. Cl.
*E21B 49/08* (2006.01)
*E21B 49/00* (2006.01)
*B65B 63/00* (2006.01)

(52) U.S. Cl.
CPC ............ *E21B 49/086* (2013.01); *B65B 63/00* (2013.01); *E21B 49/005* (2013.01)

(58) Field of Classification Search
CPC ...... E21B 49/00; E21B 49/086; E21B 49/005; G01N 1/04; G01N 1/08; B65G 65/02; B65B 63/00; G01L 1/20
USPC ....................................................... 73/152.23
See application file for complete search history.

(56) References Cited

U.S. PATENT DOCUMENTS

| | | | | |
|---|---|---|---|---|
| 2,369,582 A * | 2/1945 | Lewis | ....................... | B07B 1/38 134/140 |
| 2,950,724 A * | 8/1960 | Roederer, Jr. | ........... | E21B 49/02 134/183 |
| 3,135,685 A * | 6/1964 | Tanner | .................. | E21B 21/065 175/206 |
| 3,563,255 A * | 2/1971 | Morris | ................... | B01D 35/20 134/133 |
| 3,811,518 A * | 5/1974 | Kalaf | ....................... | E21B 21/07 175/206 |
| 6,386,026 B1 * | 5/2002 | Zamfes | ................. | E21B 21/065 175/44 |
| 6,845,657 B2 * | 1/2005 | Williams | ................. | G01N 1/08 175/20 |
| 8,950,510 B2 * | 2/2015 | Bender | .................... | E21B 21/06 175/66 |
| 9,651,461 B2 * | 5/2017 | Snape | ........................ | G01N 1/34 |
| 2011/0277798 A1 * | 11/2011 | Hillier | ................... | E21B 21/066 134/135 |
| 2014/0137715 A1 * | 5/2014 | Sneyders | ................. | G01N 1/06 83/24 |

* cited by examiner

*Primary Examiner* — Harshad R Patel
*Assistant Examiner* — Octavia Hollington

(57) ABSTRACT

A system for automated collection of cutting samples produced during the drilling of a well includes an automated valve system for periodically collecting samples including fluid and cuttings from a flow line from a drilling rig and a packaging system for packaging each sample collected from the flow line. The packaging system deposits each sample received from the valve system at a corresponding point along a moving elongated strip of base material, covers the elongated strip of base material and samples deposited on the base material with a strip of cover material, and advances the covered elongated strip of base material and covered samples onto a reel.

17 Claims, 7 Drawing Sheets

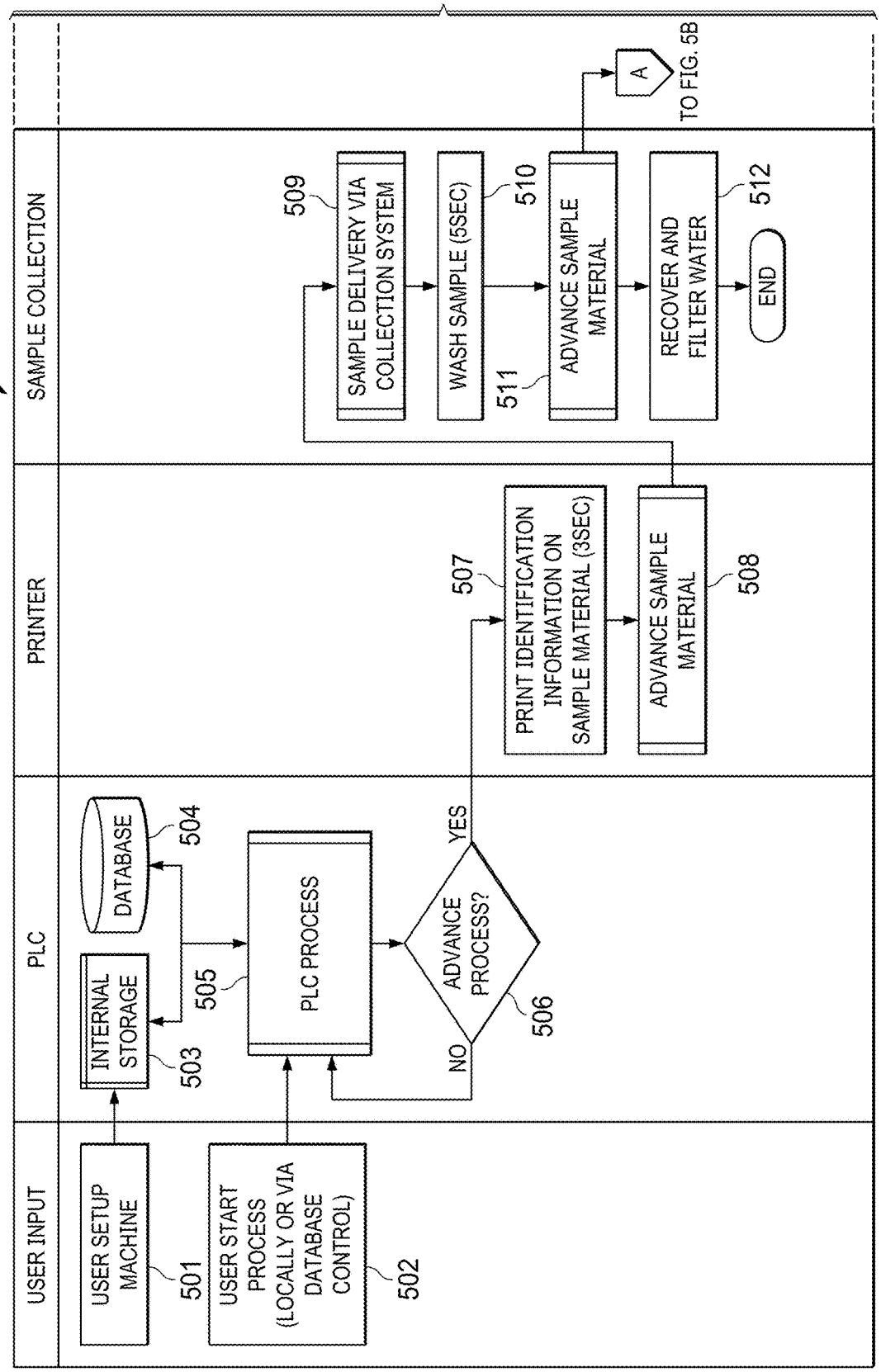

SYSTEMS AND METHODS FOR COLLECTING CUTTING SAMPLES DURING OIL AND GAS DRILLING OPERATIONS

CROSS-REFERENCE TO RELATED APPLICATION

The present application claims the benefit of U.S. Provisional Application Ser. No. 62/082,658, filed Nov. 21, 2014, and U.S. Provisional Application Ser. No. 62/215,840, filed Sep. 9, 2015, both of which are incorporated herein by reference for all purposes.

FIELD OF INVENTION

The present invention relates in general to oil and gas drilling operations and in particular to systems and methods for collecting cutting samples during oil and gas drilling operations.

BACKGROUND OF INVENTION

When an oil or gas drilling rig is drilling a well, geologists employ a human "mudlogger" to go to the well site and provide analysis of the cutting samples and well gases being produced. From the cutting samples and well gases, the geologists can identify the depths (zones) where the oil and/or gas are located.

The cutting samples are currently gathered by the mudlogger by placing a cup under the end of the flow line, which generally is a 8"-12" wide pipe going from the drilling rig to a set of mud pits. The mudlogger then hand carries these samples 30 or more yards to the mudlogger's trailer where the samples are prepared/labeled for analysis, after which the mudlogger returns to the end of the flow line to collect the next set of samples.

As the efficiency of new diamond-based drilling bits has increased drilling speeds, the difficulty of the mudlogger's job of collecting cutting samples has also increased. For example, in the early 2000's, the geologists typically requested that samples be collected for every 5'-10' of drilling; however, due to the increased drilling speeds, a mudlogger currently has a difficult time just collecting samples for every 30' of drilling.

SUMMARY OF INVENTION

The principles of the present invention are embodied in a system for automated collection of cutting samples produced during the drilling of a well. In a first cycle, an automated valve collects a sample of fluid, including cutting samples, from a flow line from a drilling rig. During a second cycle, the automated valve transfers the sample of fluid to a conduit. A pump moves the sample of fluid through the conduit to a machine, which seals the cuttings from the sample in a package and optionally labels the package.

Embodiments of the present principles realize substantial advantages over the existing art including: (1) the ability to take more frequent cutting samples, even as drilling speeds increase; (2) with more frequent samples, allow for the identification of smaller oil and gas zones subsurface; (3) reduce the need for on-site human labor; (4) optionally allow for the storage of the cutting samples along with the collected liquid, which maintains sample integrity over a longer period of time; and (5) allow for the collection and storage of well gas samples along with the cutting samples.

BRIEF DESCRIPTION OF DRAWINGS

For a more complete understanding of the present invention, and the advantages thereof, reference is now made to the following descriptions taken in conjunction with the accompanying drawings, in which:

FIGS. 5A-5B are a flow diagram illustrating a preferred automated flow line sample collection and packaging process embodying the principles of the present invention.

DETAILED DESCRIPTION OF THE INVENTION

The principles of the present invention and their advantages are best understood by referring to the illustrated embodiment depicted in FIGS. 1-5 of the drawings, in which like numbers designate like parts.

Figure 1:
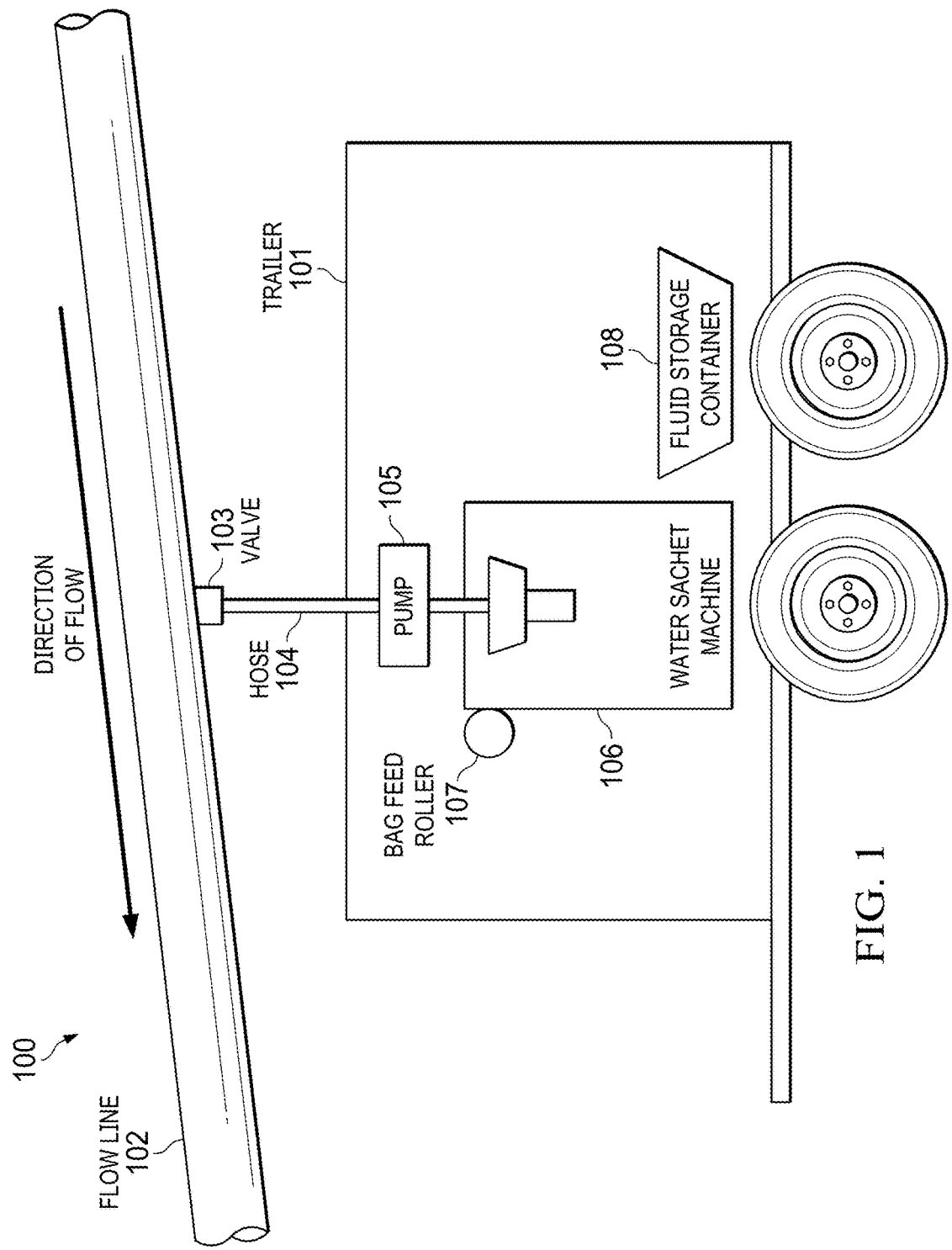
FIG. 1 is a block diagram of a first Flow Line Automated Sample Collector (FLASC) system embodying the principles of the present invention.
Figure 2:
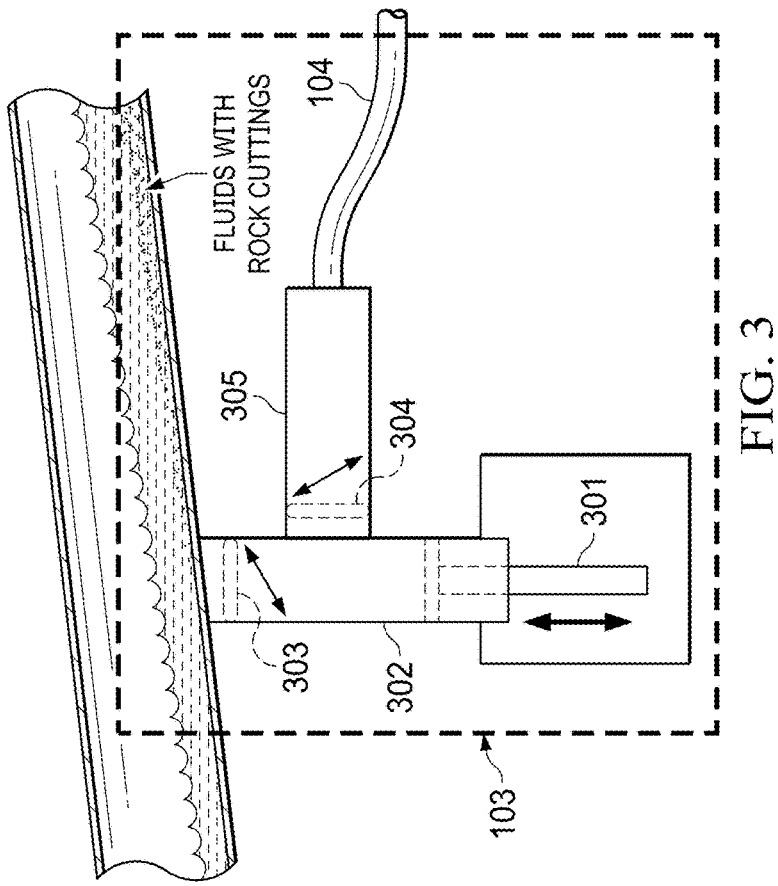
FIG. 2 is a block diagram emphasizing the flow line sample collection point shown in FIG. 1.
Figure 3:
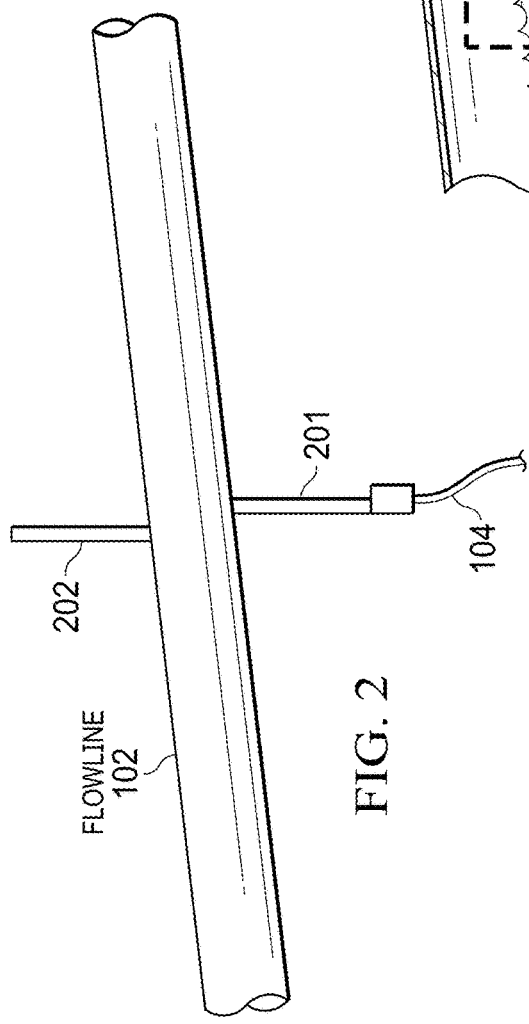
FIG. 3 is a block diagram emphasizing the sample collection valve system shown in FIG. 1.
Figure 4A:
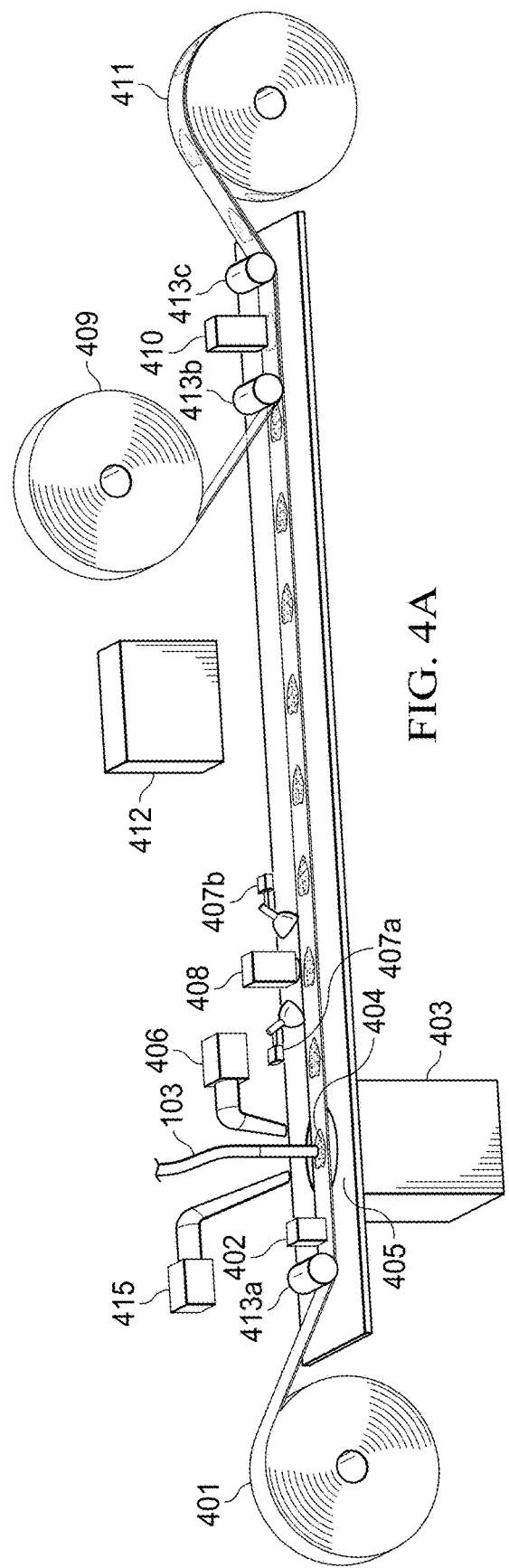
FIGS. 4A-4D are diagrams of a sample packaging system suitable for use in the FLASC system of FIG. 1 and embodying the principles of the present invention.
Figure 4B:
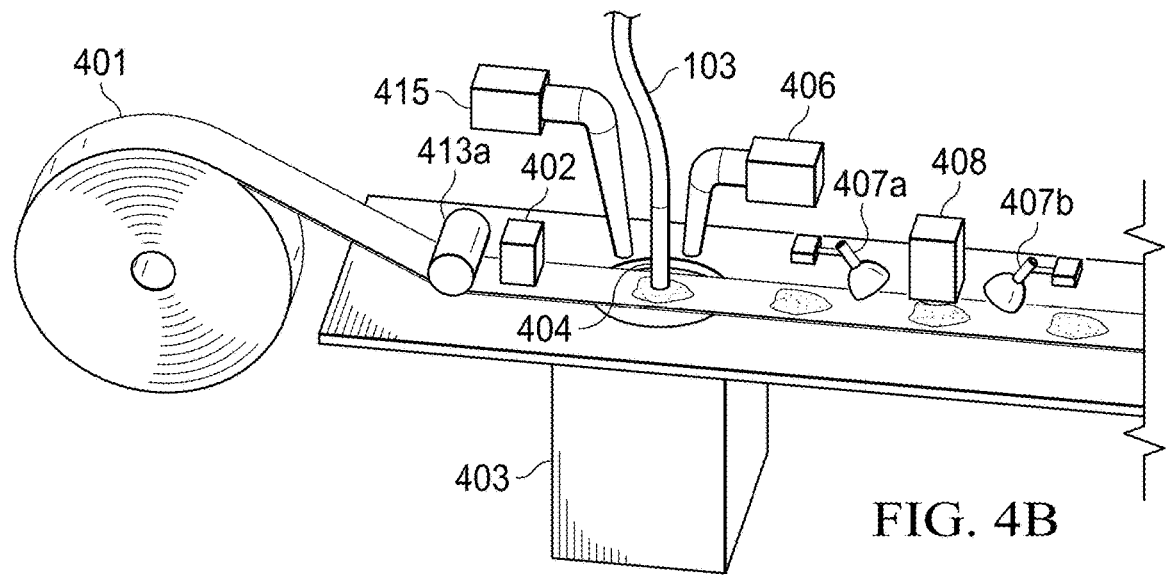
Figure 4C:
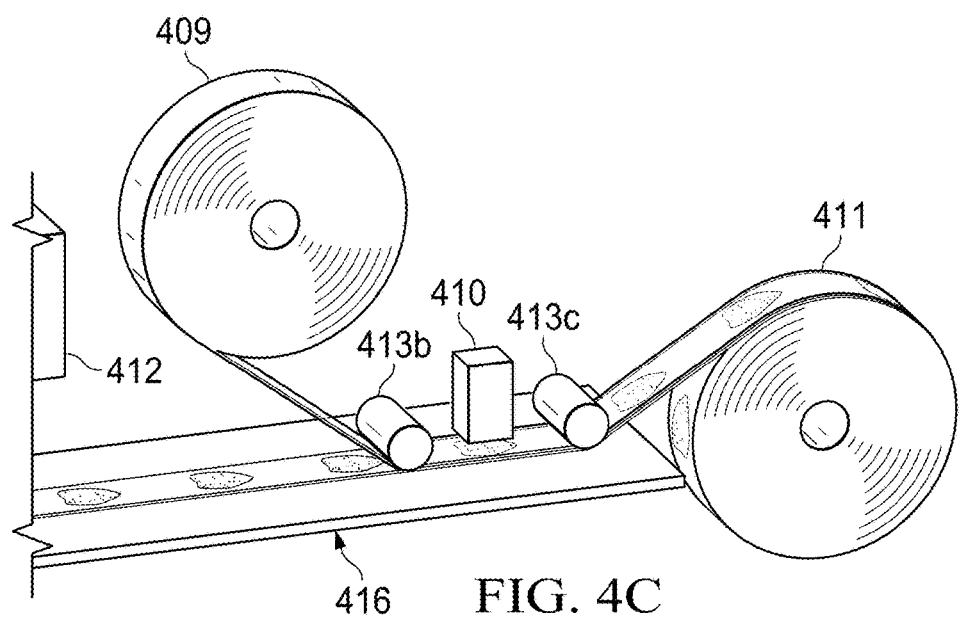
Figure 4D:
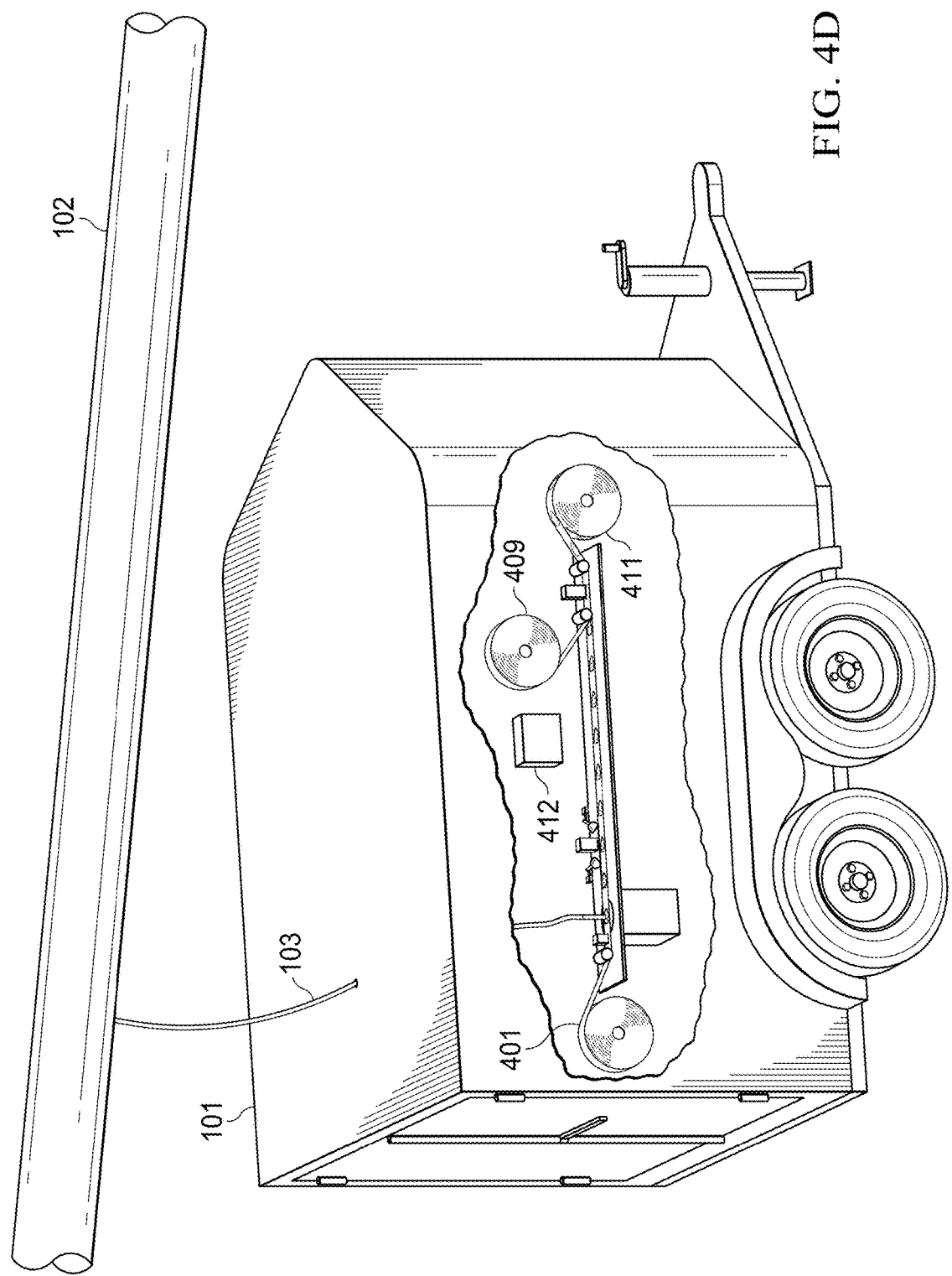

FIG. 1 is a diagram of an exemplary FLASC (Flow Line Automated Sample Collector) system 100 according to one embodiment of the principles of the present invention. FIG. 2 shows the flow line sample collection point of FIG. 1 in further detail, while FIG. 3 shows sample collection valve system of FIG. 1 in further detail.

Generally, the illustrated embodiment of FLASC system 100 implements a four-stage automated collection process, which advantageously allows for the collection of 5'-10' drilling samples during high-speed drilling, which is typically beyond the capability of a single human mudlogger. Preferably, FLASC system 100 is transportable, via a trailer 101 (e.g., 4' by 6' travel trailer), or similar movable platform.

In the cutting sample extraction stage, an automated valve system 103, under computer control, extracts samples through a 2" wide nipple 201 (FIG. 2) extending from flow line 102. As shown in FIG. 2, flow line 102 is also provided with a nipple 202 for gas collection, which may also be automated. More particularly, a system controller (discussed further below in conjunction with FIGS. 4A-4D), which interfaces with the conventional depth finder device on the associated drilling rig, is programmed to extract the samples after a set amount of footage is drilled. For example, if set for 10' in the program, then with every 10' drilled, sample cuttings are extracted through automated valve 103.

In the preferred embodiment, automated valve system 103 includes a piston-actuated valve, which operates similar to a hypodermic needle withdrawing liquid from a vial. In the preferred embodiment shown in FIG. 3, valve system 103 includes a piston 301 moving within a cylinder 302, seals 303 and 304, and reservoir 305. Seal 303 opens when piston 301 retracts away from flow line 102, to allow fluid and rock cuttings to flow into cylinder 302, and closes when piston 301 pushes back towards flow line 102. Conversely, seal 305 closes when piston 301 retracts away from flow line 102 and opens in response to fluid pressure as piston 301 pushes Fluid back towards flow line 102, thereby allowing the fluid and rock cuttings to move from cylinder 301 and into reservoir 305 and on into a 1" poly-flow line (hose) 104 leading to the transportation stage. In the illustrated embodiment, at each sample point, automated valve 103 withdraws 4-ounces of fluid and cuttings from flow line 102 into reservoir 305, although this amount may vary in actual applications.

In transportation stage, the sample of liquids and cuttings pass through poly-flow line 104 to an automated bag-and-tag apparatus within trailer 101. Trailer 101, which is located ideally directly under flow line 102 during logging operations, also includes a pump 105 for drawing fluids and cuttings through poly-line 104 under pressure. Pump 105 is preferably powered by rig electricity and a pin-prick hole on the top of poly-flow line 104 preferably assists with the pressure.

In the bag and tag stage, the fluid and cuttings move to a modified sachet machine 106 housed in trailer 101. The system controller causes the sachet machine to move the sample down a line to bagging area where a durable plastic "form-and-seal" bag receives the 4-ounces of collected fluids, a heating element seals the open end of the bag, and a cutting device makes a single cut to create the bottom for the next sachet (bag). An ink jet printer places a label (i.e., tag) containing such information as the time, date, series number, and footage along the well bore where the sample was collected onto the plastic bag.

Once stamped, the bagged cuttings sample is moved to the reservoir stage, where the stamped sample bag is pushed by way of a simple lever into a fluid storage container 108, where it is stored with previously collected samples until a technician arrives to collect the sachets every few days.

FIGS. 4A-4D illustrate another particular bag and tag system 400 suitable for use in FLASC system 100 of FIG. 1. In bag and tag system 400, a reel or similar feed mechanism provides a strip of sample material 401, which in one preferred embodiment is Kevlar mesh, which filters out unwanted materials (e.g., the liquids provided by poly-line 104), but retains the desired materials (e.g., the cuttings). In the illustrated embodiment, material strip 401 is approximately four inches (4") wide and is supplied from an approximately two foot (2') roll.

Material strip 401 advances to an optional printer 402, which prints information such as the time, date, series number, and footage along the well bore where the sample was take. Material strip 401 advances again, and a sample 404 is applied from poly-line 104 to a corresponding point on material strip 401 at station 405, shown in detail in FIG. 4B. The sample is then washed by washer 415 with water or another cleaning fluid and dried with a wireless blower 406. The cleaning Fluid and removed drilling liquids are captured in catch basin 403 for later removal and disposal (e.g., by a bilge pump or hose).

The dried sample next advances to an image station 405 (FIG. 4B) including a digital camera 408, visible light source 407a, and ultraviolet light source 407b. Digital camera 408 takes conventional and black-light digital images of the sample, which are sent via system controller 412 to a remote server (not shown) for use in generating mud logs in real time.

The sample then moves to a covering/packaging station 416 (FIG. 4C) where it is covered by a material 409 such as an adhesive-backed tape, cellophane, finer mesh Kevlar provided by a reel or similar dispenser. Preferably, cover material 409 includes an adhesive backing that seals directly to the face of base material 401 under pressure. However, in an alternate embodiment, a ultrasonic welder 408 or similar device seals material strip 401 and cover material 409 together around the periphery of each sample.

The sample finally advances on to reel 411 where it is stored with other packaged samples until the entire reel is removed by a technician. Depending on the mesh size of base material 401 and/or cover material 409, the sample may dry further, which makes the packing of samples on reel 411 tighter and reel 411 lighter.

Controller 412, which is preferably based on a programmable logic controller (PLC), controls sample packaging process, as well as the sample collection through valve 103, as discussed above. In one particular embodiment, controller 412 moves the samples through bag and tag system 400 in four inch (4") increments, although the movement increments may a vary in actual embodiments. In addition, controller 412 provides a wireless or wired communications interface with an external server for transmitting the real-time sample images discussed above.

In the illustrated embodiment, tension rollers 413a-413c provide tension to material strip 401, as well as guide material strip 401 as it moves through the bag and tag process.

Figure 5B:
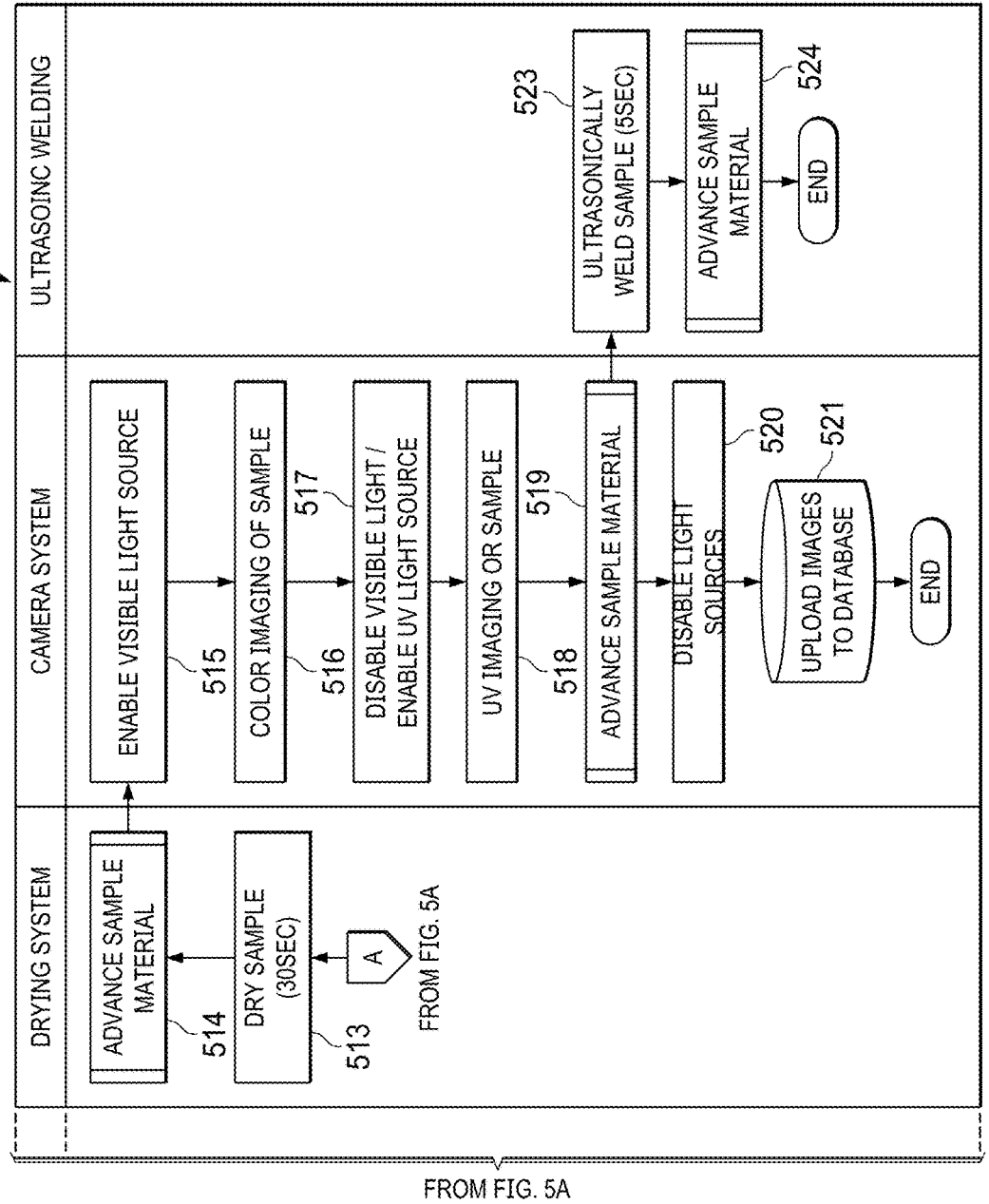

FIGS. 5A and 5B illustrate a preferred sample collection and packaging procedure 500 based on bag and tag system 400 of FIGS. 4A-4D. At Block 501, the user sets-up internal data storage 503 within controller 412 and initializes communications with an external database 504. At Block 502, the user initiates the collection and packaging process by triggering processing by a programmable logic controller (PLC) 505 within controller 412.

When the system is ready, PLC 505 advances sample material 401 and identification information is optionally printed at a selected location (Block 507), after which base material 401 again advances (Block 508). At Block 509, a sample is delivered to a selected spot on sample material 401 from poly-line 104. The collected sample is then washed, at Block 510, and the washing fluid and drilling fluid flushed from the sample collected in catch basin 403 (Block 512). Dryer 406 dries the sample at Block 513.

PLC 505 advances sample material 401 further at Block 514. Visible light source 407a is enabled at Block 515 and at Block 516, camera 408 takes a color image of the sample. Visible light source 407 is disabled and ultraviolet light source 407b is enabled (Block 517), which allows camera 408 to take an ultraviolet image of the sample (Block 518).

At Block 519, PLC 505 advances sample material 401 for sealing. The visible light and ultraviolet images taken of the sample are uploaded to the database (Block 521) to the external database 504. The sample is covered by cover material 409 and sealed between base material 401 and cover material 409. In one preferred embodiment, the strip of cover material 409 has an adhesive backing that directly adheres to the face of the strip of base material 401 as the two strips come into contact as they travel through tension rollers 413a and 413b. Preferably, the adhesive backing adheres to the base material 401 around the entire periphery of each cutting sample such that each cutting sample is disposed within it own pouch or sachet.

In one alternate embodiment, a housing 410 houses an ultrasonic welder, which seals the strip of cover material 409 to the strip of base material 401. In another alternate embodiment, housing 410 includes an x-ray fluorescent (XRF) analysis unit, either alone or along with the ultrasonic welder. Finally, the sample is advanced by PLC 505 onto storage roll 411 or other suitable storage system.

One advantage of bag and tag system 400, which employs either adhesive-backed cover material 409 and/or an ultrasonic welder 410, is a reduction of an explosion risk over a form-seal system discussed above in conjunction with the embodiment of FIG. 1. As an initial matter, the heating element of a typical vertical form-fold-seal system takes times to heat up, which either delays the packaging of samples or causes a failure of the earliest collected cutting samples to properly package. More importantly, system 100 may be used in the proximity of a drilling rig blow-out preventer, where the sealing system heating element could be in the presence of highly explosive $H_2S$ gas occurring naturally in the sub-surface. An ultrasonic welder, which does not employ a heating element and operates at low electrical wattages, advantageously reduces the risk of $H_2S$ gas explosions.

Advantageously, the FLASC system allows for the collection of more frequent samples and the easier identification of smaller zones, which were previously hidden when only 30' samples were capable of being collected. In turn, a geologist can work more effectively and efficient in analyzing a drill hole. In addition, in some embodiments, where the cutting samples are collected and stored in a durable plastic bag along with an amount of collected liquid, the cutting sample integrity is increased over current techniques, where the cutting samples are typically collected in a cotton bag and dried out. Also, since the samples may be collected in a plastic bag, the gasses produced by the cuttings provide an alternate way to retrieve gas readings that can be added to the value of service.

In general, the drilling industry has not been motivated to pursue automated cutting sample collection, fearing that it may devalue the worth of having a person subjectively offering their interpretation of the samples. Also, the industry has accepted that 30' samples are good enough, although they would prefer more frequent samples collected. By use of the FLASC system, companies can meet the needs of a customer in providing valuable data for analysis.

Although the invention has been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiment disclosed might be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiments that fall within the true scope of the invention.

What is claimed is:

1. A system for automated collection of cutting samples produced during the drilling of a well comprising:
    an automated valve system for periodically collecting samples including fluid and cuttings from a flow line from a drilling rig;
    a packaging system for packaging each sample collected from the flow line, the packaging system operable to:
        deposit each sample received from the valve system at a corresponding point along a moving elongated strip of base material;
        cover the elongated strip of base material and samples deposited on the base material with an elongated strip of cover material; and
        advance the covered elongated strip of base material and covered samples onto a reel.

2. The system of claim 1, wherein the automated valve system includes a hose and a valve operable to:
    in a first cycle, draw a sample from the flow line; and
    in a second cycle, transfer the sample to the hose.

3. The system of claim 2, wherein the automated valve comprises:
    a piston for drawing a sample from the flow line through a first seal into a chamber during the first cycle and for forcing the sample from the chamber into the hose through a second seal during the second cycle.

4. The system of claim 1, wherein the packaging system is operable to cover the elongated strip of base material with the elongated strip of cover material having an adhesive backing for sealing the samples between the strip of base material and the strip of cover material.

5. The system of claim 1, wherein the packaging system is further operable to wash and dry each sample deposited on an elongated strip of base material prior to covering the elongated strip of base material and samples deposited on the elongated strip of base material with the elongated strip of cover material.

6. The system of claim 1, wherein the packaging system is further operable to image each sample deposited on the elongated strip base material prior to covering the elongated strip of base material and samples deposited on the elongated strip of base material with the elongated strip of cover material.

7. A method of collecting cutting samples from a drilling rig flow line comprising:
    periodically collecting samples including fluid and cuttings from the drilling rig flow line;
    periodically depositing the samples along an elongated strip of mesh material such that the fluid drains and the cutting samples remain on the strip of mesh material;
    covering the elongated strip of mesh material and the cutting samples on the strip of mesh material with an elongated strip of cover material; and
    advancing the covered elongated strip of base material and covered cutting samples onto a reel.

8. The method of claim 7, wherein the elongated strip of cover material comprises an adhesive backing for adhering the elongated strip of cover material to the elongated strip of mesh material.

9. The method of claim 8, wherein a portion of the elongated strip of cover material adheres to a corresponding portion of the elongated strip of base material around a periphery of each sample.

10. The method of claim 7, further comprising adhering a portion of the elongated strip of cover material to a corresponding portion of the elongated strip of base material around a periphery of each sample using an ultrasonic welder.

11. The method of claim 7, further comprising washing and drying each cutting sample prior to covering the elongated strip of mesh material and the cutting samples.

12. The method of claim 7, further comprising taking a visible light image of each sample prior to covering the elongated strip of mesh material and the cutting samples.

13. The method of claim 7, further comprising taking an ultraviolet image of each sample prior to covering the elongated strip of mesh material and the cutting samples.

14. The method of claim 7, further comprising storing the covered elongated strip of mesh material and the cutting samples on the reel.

15. The method of claim 7, wherein periodically collecting samples including fluid and cuttings from the drilling rig flow line comprises:

during a first cycle, drawing a sample from the flow line through a first seal into a chamber with a piston; and during a second cycle, forcing the sample from the chamber into the hose through a second seal with the piston.

16. A system for packaging drilling cutting samples comprising:

a processing path along which an elongated strip of base material moves;

a depositing station disposed along the processing path for periodically depositing cutting samples at points along the strip of base material moving along the processing path;

a washing and drying station disposed along the processing path for washing and drying cutting samples deposited on the elongated strip of base material moving down the processing path;

an imaging station disposed along the processing path for taking at least one image of the cutting samples deposited on the elongated strip of base material moving down the processing path;

a packaging system for packaging each sample collected from a flow line by covering the elongated strip of base material and samples deposited on the base material with an elongated strip of cover material and advancing the covered elongated strip of base material and covered samples onto a reel.

17. The system of claim 16, further comprising a printer for periodically marking the strip of base material for identifying the samples deposited on the strip of base material moving down the processing path.

* * * * *